United States Patent [19]

Engel

[11] 4,251,675

[45] Feb. 17, 1981

[54] PREPARATION OF DIPHENYLMETHANE

[75] Inventor: Dusan J. Engel, Des Plaines, Ill.

[73] Assignee: UOP Inc., Des Plaines, Ill.

[21] Appl. No.: 21,043

[22] Filed: Mar. 15, 1979

[51] Int. Cl.$^2$ ............................................. C07C 15/16
[52] U.S. Cl. ................................... 585/422; 585/446; 585/454; 585/469
[58] Field of Search ................................ 585/469, 422

[56] References Cited

U.S. PATENT DOCUMENTS

| | | | |
|---|---|---|---|
| 3,006,972 | 10/1961 | Fields et al. | 585/422 |
| 3,079,448 | 2/1963 | Jenny | 585/422 |
| 3,833,677 | 9/1974 | Grard | 585/422 |

OTHER PUBLICATIONS

M. Robert Jenny, Comptes Reuda 250, 1659–1661, 1960.

*Primary Examiner*—Veronica O'Keefe
*Attorney, Agent, or Firm*—James R. Hoatson, Jr.; Raymond H. Nelson; William H. Page, II

[57] ABSTRACT

Diphenylmethane is synthesized by reacting benzene and benzyl chloride at elevated temperatures in a Friedel-Crafts type reaction using catalytic amounts of a Friedel-Crafts metal halide catalyst such as ferric chloride whereby the desired product is obtained with a good selectivity and a high conversion rate.

1 Claim, No Drawings

PREPARATION OF DIPHENYLMETHANE

BACKGROUND OF THE INVENTION

It is known in the prior art that aromatic compounds which are rich in electrons, such as those which contain various substituents on the aromatic ring, may be reacted in Friedel-Crafts type reaction. For example, benzophenone may be synthesized by reacting benzene plus benzoyl chloride, benzoic anhydride or benzoic acid in the presence of metal halides such as aluminum chloride, titanium tetrachloride, antimony pentachloride, molybdenum pentachloride, etc. However, it has been reported in the prior art that a combination of aluminum chloride with ferric chloride as the catalyst gave a detrimental action to obtaining desired yields of benzophenone. However, the catalysts which are used in this reaction are present in stoichiometrical amounts, thus adding to the cost of the desired product.

It has also been reported in the literature that ferric chloride may be used as a catalyst for Friedel-Crafts reactions involving benzene. However, the ferric chloride was always present in stoichiometric amounts when used as a catalyst for reactions involving benzene, due to the relative unreactiveness of the benzene, which is an electron poor aromatic compound. In constradistinction to this, when using electron rich aromatic compounds such as toluene, the isomeric xylenes, anisole, etc., wherein the benzene is provided with a reactive substituent, it is possible to use ferric chloride in less than stoichiometric amounts. For example, U.S. Pat. No. 3,933,917 discloses a process for the production of dimethylbenzophenone. However, the starting material for the preparation of this compound consists of a highly substituted benzene. The reference teaches that a dimethylbenzene such as m-xylene or o-xylene is butylated to obtain a highly activated t-butyl dimethylbenzene, and, therefore, the reaction can employ relatively small amounts of ferric chloride as a catalyst due to the electron rich tri-substituted benzene. Thereafter, when the benzoylation has been effected, the intermediate compound is then debutylated by means of aluminum chloride to form the desired product. Other references which have been found in the literature also disclose processes for the benzoylation of aromatic compounds. In this respect, it is noted that in the *Journal Of The American Chemical Society*, Volume 80, pages 2296-2300 the relative rates of aluminum chloride catalyzed benzoylation of benzene derivatives is set forth. Table I on page 2297 of the *Journal* sets forth the rate constants and compares the relative rates of benzene with substituted benzenes. The benzoylation rates which are given disclose that benzene has a relative rate of 1.00 and chlorobenzene has a relative rate of 0.0115. As opposed to this, other substituted benzenes such as toluene shows a relative rate of reaction of 110 while the xylenes have relative rates ranging from 140 for p-xylene up to 3940 for m-xylene. Even while utilizing aluminum chloride, which is a more active catalyst than ferric chloride, the table would teach away from the reaction of the present invention in which it has been discovered that benzene, which is an electron poor compound, may be benzylated in the presence of a catalytic amount of ferric chloride. Likewise, a Russian reference, namely Yuldashev et al in Nauch. Tr. Taschkent Univ., 1972, No. 419, pages 176-179 discloses that cinnamoyl chloride did not react with toluene, which, as hereinbefore set forth is more reactive than benzene, in the presence of a catalytic amount of ferric chloride. As another indication of the relative inactivity of an unsubstituted aromatic compound such as benzene, H.C. Brown in the *Journal of Organic Chemistry*, Volume 23, pages 414-416 discloses on page 415 that when using nitrobenzene as a solvent, benzene has a relative rate of only 1/154 as compared to the rate of toluene which has been given a relative rate of 1.00 in a benzoylation reaction. The same author in the *Journal Of The American Chemical Society*, Volume 81, pages 3308-3310 also discloses at Table 2 in page 3309 when using ethylene chloride or benzoyl chloride as the solvent, the benzene is relatively inactive as opposed to toluene and the xylenes in a benzoylation reaction. These references would also teach away from the process of the present invention, that is, that benzene may be reacted with a benzyl halide in the presence of a catalytic amount of ferric chloride inasmuch as benzene is an unreactive or electron poor aromatic compound.

This invention relates to a process for synthesizing diphenylmethane by reacting benzene with a benzyl halide in the presence of a catalytic amount of a Friedel-Crafts catalyst.

The desired product of the present invention comprises diphenylmethane which is a precursor to benzophenone. The latter product can be synthesized from diphenylmethane by an air oxidation step using an organometallic complex in a catalytic amount. However, heretofore this was not a preferred method inasmuch as it has been relatively expensive to prepare diphenylmethane. By utilizing the process of the present invention, it is possible to obtain diphenylmethane in a relatively inexpensive manner, thus considerably lowering the cost of preparing the desired product.

Benzophenone is a compound which is assuming increasing importance in the chemical industry. This compound, namely, benzophenone, is used in perfumery due to its mild aromatic and fixitive properties. In addition to its use in perfumery, it also finds use as an anthelmintic, bacteriostatic agent, as well as a fungicide and insecticide. In industry it is also used as an intermediate for various processes, for discoloration of petroleum waxes and for copolymerization of drying oils and styrene monomer. Lately, it has become used to a great extent in ultra-violet cured coatings and inks as a photoinitiator.

It is therefore an object of this invention to provide an improved process for the preparation of diphenylmethane.

A further object of this invention is to provide a process for synthesizing diphenylmethane by reacting benzene with a benzyl halide in the presence of certain Friedel-Crafts catalysts.

In one aspect an embodiment of this invention resides in a process for the preparation of a diphenylmethane which comprises reacting benzene with a benzyl halide in the presence of a catalytic amount of a Friedel-Crafts metal halide at reaction conditions, and recovering the reactant diphenylmethane.

A specific embodiment of this invention is found in a process for the preparation of diphenylmethane which comprises reacting benzene with benzyl chloride in the presence of a catalytic amount of anhydrous ferric chloride at a temperature in the range of from about 50° to about 150° C. and a pressure in the range of from about atmospheric to about 100 atmospheres, and recovering the desired diphenylmethane.

Other objects and embodiments will be found in the following further detailed description of the present invention.

As hereinbefore set forth, the present invention is concerned with the process for preparing or synthesizing diphenylmethane by reacting benzene with a benzyl halide in the presence of a Friedel-Crafts metal halide catalyst. In the preferred embodiment, the Friedel-Crafts metal halide catalyst which is employed will comprise ferric chloride, said catalyst being present in catalytic amounts which are less than stoichiometric amounts, the latter having heretofore been required when attempting to react a relatively inert aromatic compound such as benzene or chlorobenzene which are electron poor. By utilizing ferric chloride in an anhydrous state and also by using elevated temperatures, it has now been found possible to employ catalytic amounts of the metal halide rather than the stoichiometric amounts which heretofore have been equired. The reaction is effected at elevated temperatures in the range of from about 50° to about 150° C,; and while in the preferred embodiment of the invention the Friedel-Crafts type reaction is effected at atmospheric pressure, it is also contemplated within the scope of this invention that superatmospheric pressure ranging up to about 100 atmospheres may be employed, the preferred pressure being that which is sufficient to maintain a major portion of the reactants in the liquid phase. By utilizing these conditions, as well as by employing anhydrous ferric chloride, it is possible to obtain yields of the desired product of greater than 75% while the selectivity to the desired product will also exceed 75%. In addition to the aforementioned parameters of temperature and pressure, other reaction conditions which are employed will include residence times which may range from about 0.5 up to about 12 hours or more in duration and the presence of an inert atmosphere, if so desired, such as nitrogen, helium, argon, etc.

The mole ratio of the components of the reaction may vary over a relatively wide range, the benzene being present in a molar excess over the benzyl halide. In the preferred embodiment of the invention, the benzene will thus be present in the reaction mixture in a mole range of from about 10:1 to about 20:1 moles of benzene/mole of benzyl halide. Likewise, the Friedel-Crafts metal halide catalyst will also be present in the reaction mixture in a relatively small catalytic amount. For example, the mole ratio of Friedel-Crafts metal halide catalyst to benzene will be in a ratio of from about 0.0001:1 to about 0.0003:1 moles of catalyst/mole of benzene and from about 0.001:1 to about 0.003:1 moles of catalyst/mole of benzyl halide. It is thus apparent that by being able to use such a relatively small amount of catalyst it is possible to lower the cost of preparing the desired compound, namely, diphenylmethane with a concurrent lower cost of preparing benzophenone.

In the preferred embodiment of the invention the benzyl halide which may comprise benzyl chloride, benzyl bromide, benzyl iodide which is utilized as one of the reactions in the process of this invention, is added to the benzene and catalyst, the addition being accomplished during a period which may range from about 0.1 to about 10 hours, and preferably in a range of from about 0.1 to about 2 hours. If so desired, as hereinbefore set forth, the reaction may be effected in an inert atmosphere. When utilizing a residence time in the upper range hereinbefore set forth, it is desirable to use this inert atmosphere in order to counteract the presence of the hydrohalic acid such as hydrochloric acid which is evolved during the reaction and which may act in a deleterious manner as a catalyst for any side reactions which may occur during the condensation. When utilizing this inert atmosphere, it may be employed as a purge by bubbling the gas such as nitrogen through the reactants to entrap the hydrogen halide and remove the same from the reaction vessel or, if so desired, the inert atmosphere may also be employed as a blanket. However, in the preferred embodiment in the invention, the former is preferred.

The process of the present invention may be effected in any suitable manner and may comprise either a batch or continuous type operation. In one embodiment of the invention, the two reactants comprising the benzyl halide and benzene are placed in a reaction vessel such as a flask which may be equipped with a thermometer, stirring means, condenser, nitrogen inlet line, if so desired, etc. The anhydrous ferric chloride is then added to the reactor which is then heated to the desired operating temperature which will be within the range hereinbefore set forth and maintained thereat for a predetermined residence time. At the end of this residence time, the heating is discontinued and the contents thereof are treated by the addition of a caustic compound such as sodium hydroxide and stirred at room temperature or, if so desired, at an elevated temperature. After extraction, the caustic layer is extracted with solvent; again the organic layers are combined, washed with water and dried over a drying agent such as sodium sulfate. The solvent is then evaporated and the residue is subjected to fractional distillation under reduced pressure or atmospheric pressure to recover the desired diphenylmethane.

As an alternative method of preparing the desired product, the reactants may be charged to the reactor which is thereafter purged with dry nitrogen and the anhydrous ferric chloride then added. Upon reaching the desired operating temperature, a slow nitrogen feed may be maintained above the liquid surface or, if so desired, the nitrogen may be bubbled through the reaction mixture while maintaining said mixture in a constant state of agitation.

In another modification of the process of the present invention, the apparatus of the type hereinbefore set forth may be purged with a dry gas and thereafter the benzene is added to said flask. Following this, the anhydrous ferric chloride catalyst is added to the flask following which the benzyl halide is slowly added thereto for a predetermined period of time. By utilizing this type of operation, the molar excess of the benzene is maintained in the desired range, whereby minimizing the formation of any undesired side products. Inasmuch as the reaction is exothermic in nature, external means for controlling the temperature of the reactor are utilized, said external means including ice baths, cooling coils, etc. Upon completion of the addition of the benzyl halide, the reaction is allowed to proceed for a period of time sufficient to complete the reaction. At the end of the reaction time, an aqueous solution of sulfuric acid (or simply water) may be added to quench the reaction while maintaining the temperature in a range of from about 50° to about 150° C. The aqueous solution may then be separated from the organic phase following which a solution of sodium carbonate, sodium sulfate, and water is added. Again, the aqueous phase is separated from the organic phase while the latter is then washed, dried and subjected to fractional distillation under reduced pressure in order to separate the desired diphenylmethane from any undesired side products which may have formed as well as unreacted starting materials. Alternatively, the product recovery may be accomplished by a direct distillation of the product mixture, first at 200-300 mm of mercury to remove benzene, and then at high vacuum (about 1 mm of mercury) to obtain diphenylmethane.

It is also contemplated within the scope of this invention that the synthesis of the diphenylmethane may be accomplished by utilizing a continuous method of operation. For example, when this type of operation is employed, a quantity of benzene and metal halide catalyst are charged to a reaction zone which is maintained at the proper operating conditions of temperature and pressure. The benzyl halide which forms the other reactant is slowly added to the reactor at a reduced rate in order to maintain an inlet excess of benzene in the reaction zone. After passage through the reaction zone for a predetermined period of time, the reactor effluent is continuously withdrawn and subjected to conventional means of separation similar in nature to those hereinbefore set forth, whereby the desired diphenylmethane may be separated and recovered from the catalysts, unreacted starting materials and/or undesired side products, the unreacted starting materials comprise benzene and benzyl halide being recycled to form a portion of the feed stock.

The following examples are given for purposes of illustrating the process of this invention. However, it is to be understood that these examples are given merely for purposes of illustration and that the broad scope of the present invention is not necessarily limited thereto.

EXAMPLE I

In this example 93.6 grams (1.2 mole) of benzene, 53.3 grams (0.4 mole) of benzyl chloride and 0.033 grams (0.0002 mole) of ferric chloride were charged to a 250 cc flask provided with a thermometer, mechanical stirring means, sampling line, and a condenser provided with water cooling means. The mixture was stirred and heated to a temperature of 65° C., hydrogen chloride being evolved at this temperature. The mixture was allowed to react for a period of 2.5 hours following which heating was discontinued and after cooling the mixture was transferred into a 200 cc flask. The mixture was then subjected to fractional distillation under reduced pressure. After removal of the benzene the desired product comprising diphenylmethane in an amount of 17.9 grams was recovered, said recovery being effected at a temperature of 85° to 87° C. at a pressure of 1.2 mm of mercury. It was determined that the selectivity to diphenylmethane was 25%.

EXAMPLE II

To illustrate the importance of having the benzene present in the reaction mixture in a molar excess of from about 10:1 to about 20:1 moles of benzene/mole of benzyl halide, another experiment was performed in which 93.6 grams (1.2 mole) of benzene, 15.7 grams (0.12 mole) of benzyl chloride and 0.026 grams (0.00016 mole) of ferric chloride were placed in an apparatus similar to that described in Example I above. The mixture was purged with nitrogen and allowed to react at a temprature of about 65° C. for a period of 2 hours. At the end of this period the reaction mixture was subjected to gas chromatography and infrared analysis. These analyses determined that there had been an 80% selectivity to diphenylmethane with a 74% conversion of the benzyl chloride.

A repeat of this experiment using the same amount of reactants plus 0.037 grams (0.00022 mole) of ferric chloride and heating the mixture to about 65° C. under a nitrogen blanket for a period of 2 hours showed, by means of gas chromatography, the 76% selectivity to diphenylmethane, 100% conversion of the benzyl chloride having been effected.

I claim as my invention:

1. In a process for the preparation of a diphenylmethane compound which comprises reacting benzene with a benzyl halide selected from the group consisting of benzyl chloride, benzyl bromide and benzyl iodide in an anhydrous reaction medium at a temperature in the range of from about 50° C. to about 150° C. and a pressure of from about 1 atmosphere to about 100 atmospheres in contact with a catalyst consisting essentially of ferric chloride, the improvement which comprises maintaining the quantity of said benzene in a molar excess of from about 10 to about 20 moles of said benzene per mole of said benzyl halide and maintaining the stoichiometric quantity of said ferric chloride in the range of from about 0.001 to about 0.003 moles of said ferric chloride per mole of said benzyl halide and from about 0.0001 to about 0.0003 moles of said ferric chloride per mole of said benzene.

* * * * *